United States Patent [19]

Stackhouse et al.

[11] Patent Number: 4,826,513

[45] Date of Patent: May 2, 1989

[54] LASER SMOKE PARTICULATE/ODOR FILTER SYSTEM

[76] Inventors: Wyman H. Stackhouse, 3201 Poinsettia Ave., Manhattan Beach, Calif. 90266; Ian M. Williamson, 555 No. Harbor Dr., Redondo Beach, Calif. 90277

[21] Appl. No.: 148,338

[22] Filed: Jan. 25, 1988

Related U.S. Application Data

[63] Continuation-in-part of Ser. No. 2,126, Jan. 12, 1987, abandoned.

[51] Int. Cl.$^4$ .............................................. B01D 50/00
[52] U.S. Cl. ........................................ 55/316; 55/387
[58] Field of Search ................... 55/316, 387, 487, 527

[56] References Cited

U.S. PATENT DOCUMENTS

| | | | |
|---|---|---|---|
| 1,789,194 | 1/1931 | Rockwell | 55/387 |
| 2,825,424 | 3/1958 | Gross | 55/316 |
| 3,526,557 | 9/1970 | Taylor | 55/487 |
| 3,877,909 | 4/1975 | Hansen | 55/487 |
| 3,944,403 | 3/1976 | Simpson et al. | 55/316 |
| 4,064,876 | 12/1977 | Mulchi | 55/316 |
| 4,236,902 | 12/1980 | Fricke | 55/316 |
| 4,448,594 | 5/1984 | Kozawa | 55/387 |
| 4,597,781 | 7/1986 | Spector | 55/126 |
| 4,619,672 | 10/1986 | Robertson | 55/316 |
| 4,619,675 | 10/1986 | Watanabe | 55/498 |
| 4,687,579 | 8/1987 | Bergman | 55/498 |

FOREIGN PATENT DOCUMENTS 2078128 1/1982 United Kingdom ................... 55/387

Primary Examiner—Bernard Nozick

[57] ABSTRACT

There is herein described an improved laser smoke particulate/odor filter including an upstream gross particulate portion that both filters and disperses the smoke, a single charcoal odor adsorption portion, a downstream particulate portion for removing smaller gross particles, and a final filtering portion for filtering out any remaining undesirable contaminated particulate. Another embodiment utilizes an upstream particulate portion that filters and disperses the smoke followed by a first and second charcoal adsorption portions of unequal sizes that are separated by a second smoke dispersion member disposed between the first and second charcoal odor adsorption portions.

10 Claims, 4 Drawing Sheets

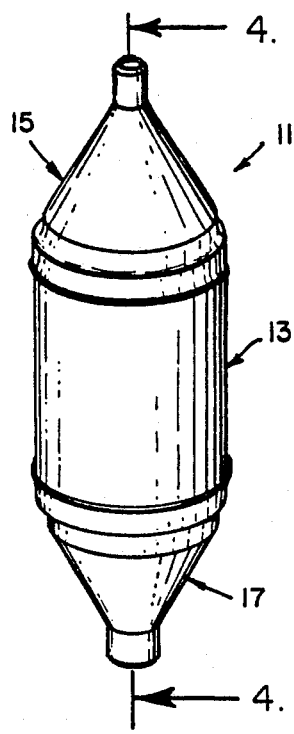
Fig. 1.
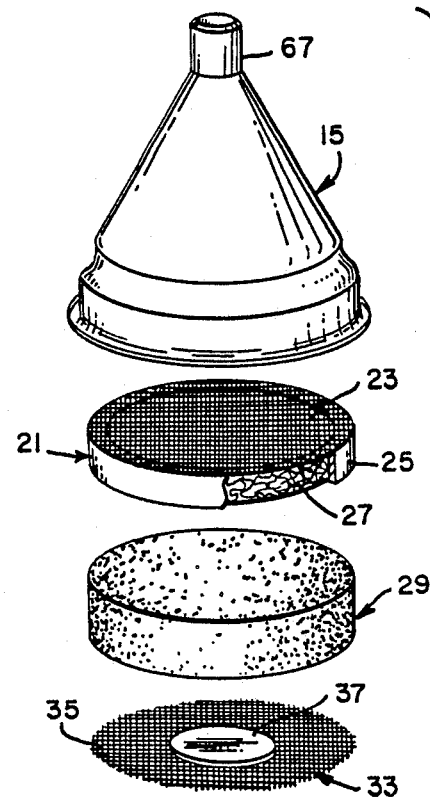
Fig. 2.
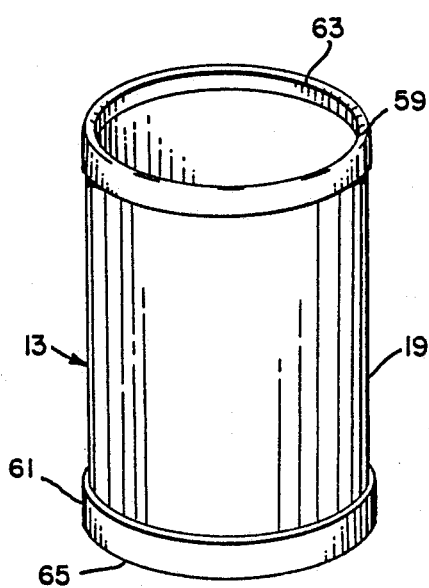
Fig. 3.
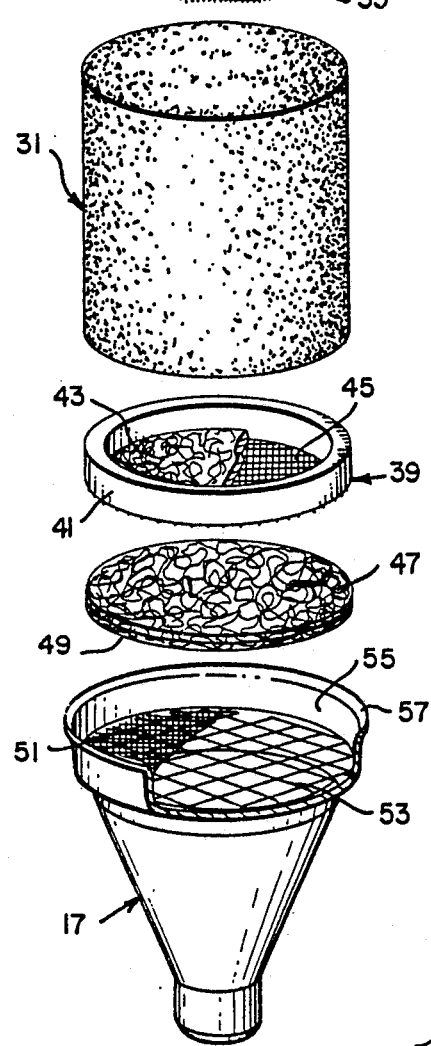

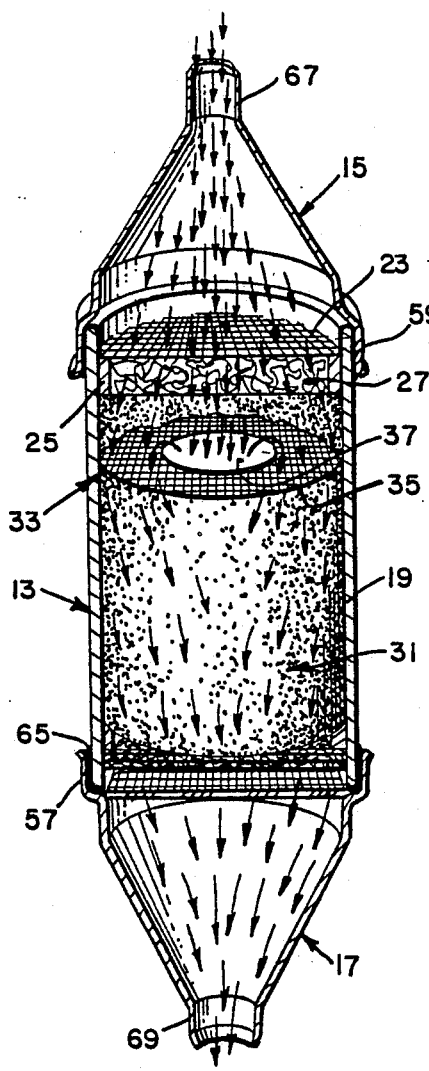
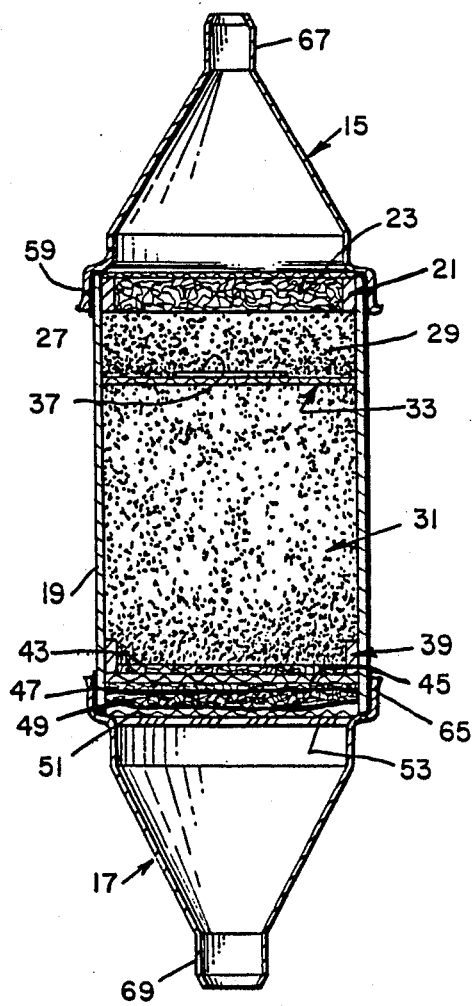
Fig. 4.
Fig. 5.

LASER SMOKE PARTICULATE/ODOR FILTER SYSTEM

This patent application is a continuation-in-part of patent application filed Jan. 12, 1987, Ser. No. 002,126 and assigned to the same assignee and now abandoned.

TECHNICAL FIELD

This invention relates to particulate and odor filters and more specifically to a laser smoke particulate/odor filter system used in a laser smoke evacuation system for surgical procedure environments wherein laser energy is being utilized.

BACKGROUND ART

The value of the laser has become recognized in various medical fields. For example, in the field of gynecology, lasers have now been utilized for cervical dysplasia, venereal warts, endometriosis, fallopian tube procedures, and vulvectomys. In the field of dermatology, laser procedures are used to port wine stain removal, tattoo removals, fungal conditions, and the removal of birth marks. Lasers are also used in podiatry for fungal nails, plantars warts, bunionectomys, and neuroma removal. Brain tumors are removed by lasers in neurosurgery, and lasers are also used in endotracheal growth vaporization and removal of carcinoma of the larynx in the pulmonary field.

One problem, however, is that laser surgery is accompanied by the generation of a large amount of smoke from irradiated tissue. In a study conducted by the Department of Otolaryngology and Public Health of Kurume University, Kurume, Japan, it was found that when there was complete vaporization of one gram of tissue, smoke particles are fifty-two times higher than the environmental standards regulated by their government agencies. From this it would appear, that without special measures being taken, the operating room air present while laser surgical procedures are being conducted will be polluted by the smoke induced by laser irradiation and to an unacceptable level.

The same study generated statistics for the following chart which shows the weight concentration relating to particle size, where the particle size is expressed as a percentage of total amount of the particles.

| Particle Diameter (Microns) | Particle Distribution (Percentage) |
| --- | --- |
| 9.0+ | 3% |
| 5.8–9.0 | 3% |
| 4.7–5.8 | 2% |
| 3.3–4.7 | 3% |
| 2.1–3.3 | 4% |
| 1.1–2.1 | 8% |
| 0.7–1.1 | 20% |
| 0.4–0.7 | 37% |
| 0–0.4 | 20% |

It can be seen from the above particle size/distribution that 77 percent of the total number of particles were less than 1.1 micron in size. According to this model, most particles in the smoke are deposited in the respiratory system at what is known in the medical field as the Alveoli level.

It is well known that there is a high correlation between carcinogenic substances and mutagenicity. Therefore, the microbial mutation tests have been made for identification of any possible carcinogenetic substances. The interpretation of the results of such tests have not been definitive, and while it cannot be said that vaporization definitely possesses carcinogenicity the possibility is high and further studies are needed.

In accordance with the present invention, an improved laser smoke particulate/odor filter system is provided whereby the possible problems heretofore alluded to in surgical environments utilizing standard air filtering means are substantially eliminated. That is, the invention provides an advantageous means to preclude contamination air (smoke plume) from the surgical site from entering the surgeon's lungs as well as those of his colleagues.

SUMMARY OF THE INVENTION

In view of the foregoing factors and conditions characteristic of the prior art, it is a primary object of the present invention to provide a new and improved laser smoke particulate/odor filter system.

Another object of the present invention is to provide a relatively simple yet effective laser smoke particulate/odor filter system which may be replaceably utilized with a conventional bypass motor/fan unit as part of a contamination control system for operating rooms.

Still another object of the present invention is to provide a unique two-in-one disposable laser smoke particulate/odor filter system.

Yet another object of the present invention is to provide a light weight and disposable laser smoke particulate/odor filter system which efficiently removes odor and particulate matter including fat, carbon, cells, microorganisms, and smoke particles which are by-products from laser surgery.

Yet a further object of the present invention is to provide an efficient and economical laser smoke particulate/odor filter system which prevents the obscuring of vision from the laser smoke plume that can cause a visual problem to a surgeon and his team, and which could possibly cause a health hazard to those who inhale such smoke.

In accordance with the present invention there is disclosed a laser smoke particulate/odor filter system usable in a laser smoke evacuation system for surgical procedure environments. The inventive concept comprises the use of of a smoke dispersion unit used in combination with a charcoal odor adsorption filter member. The dispersion unit is necessary to prevent the smoke from being concentrated in the axial center, but rather to disperse the smoke throughout the complete volume of the charcoal adsorption filter member.

In the preferred embodiment, a single particulate filter portion is located upstream and in combination with a single charcoal odor adsorption filter. The single particulate filter serves the dual purpose of filtering major particulates and also acting as a dispersion member for forcing the smoke to disperse throughout the complete charcoal adsorption portion. Research indicates that initially the flow of smoke travels axially through the filter and that the larger particulate load up the central portion of the single particulate filter which acts as a dispersion unit for the smoke flow that continues.

In accordance with another embodiment of the present invention, there is disclosed a filter system that uses a pair of charcoal adsorption portions separated by a smoke dispersion member located intermediate both charcoal filter portions. The second embodiment comprises at least one particulate filter portion, a first charcoal odor adsorption portion, a second charcoal odor adsorption portion, and a smoke dispersion member disposed between the first and second charcoal odor adsorption portions.

Preferably, the second charcoal odor adsorption portion is relatively larger than the first charcoal odor adsorption portion. The smoke dispersion member may include a screen separating the first and second odor adsorption portions, and a nonporous disk portion generally centered on the screen.

Another embodiment of the invention utilizes a foam pad filter portion as the first particulate filter portion and in which the smoke dispersion is achieved by the initial foam pad filter.

The features of the present invention which are believed to be novel are set forth with particularity in the appended claims.

The present invention, both as to its organization and manner of operation and use, together with further objects and advantages thereof, may best be understood by making reference to the following description taken in conjunction with the accompanying drawings in which like reference characters refer to like elements in the several views.

BRIEF DESCRIPTION OF THE DRAWINGS

FIG. 1 is a perspective view of the laser smoke particulate/odor filter system according to the invention;

FIG. 2 is an exploded view of a first embodiment, in perspective, of the laser smoke particulate/odor filter system shown in FIG. 1;

FIG. 3 is a perspective view of the cylindrical canister portion of the laser smoke particulate/odor filter shown in FIG. 1;

FIG. 4 is a sectional view taken along line 4—4 of FIG. 1 and illustrating the first embodiment;

FIG. 5 is an elevational view, shown in perspective section, of the laser smoke particulate/odor filter system shown in FIG. 1 and illustrating the first embodiment;

DESCRIPTION OF THE PREFERRED EMBODIMENT

Figure 6:
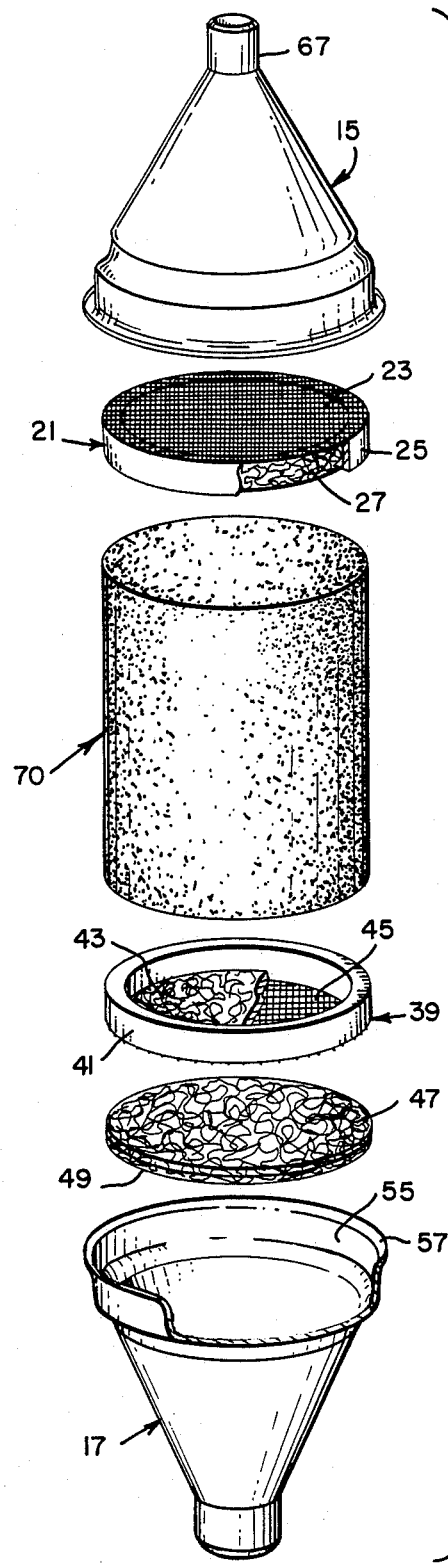
FIG. 6 is an exploded view, in perspective, of a second embodiment of the laser smoke particulate/odor filter shown in FIG. 1.

Referring now to the drawings and more particularly to FIG. 1, there is shown a laser smoke particulate/odor filter assembly 11 including a main filter body section 13, with an inlet bell 15 and an outlet bell 17.

The main filter body section 13 is best described in conjunction with views shown in FIGS. 2 and 3. As can be seen in detail, disposed within a cylindrical canister member 19 is an upstream gross particulate filter portion 21 having a plastic screen 23 mounted on a compressed paper ring 25 in which is disposed ¼ inch polyurethane pad 27. In this embodiment, the canister is about 6½ inches long and about 5 inches in diameter.

Downstream of the gross particulate filter portion 21 is disposed an approximately one inch deep first layer 29 of activated virgin coconut charcoal which is separated from an approximately four inch deep second layer 31 of activated virgin coconut charcoal by a smoke dispersion member 33. The member 33 includes an aluminum screen 35 to which is centered a nonporous smoke dispersion member 37 such as a cardboard disk, for example, and permanently mounted on the screen by any suitable means such as a suitable adhesive. However, it should be understood that a truncated cone or other configuration providing the same function can be substituted for the cardboard disk shown.

The downstream portion of the second charcoal layer 31 is retained within the cylinder 19 by a downstream gross particulate filter portion 39 which includes a ring 41, and ¼ inch polyurethane pad 43, and a plastic screen 45 disposed within the ring 41.

In contact with the screen 45 downstream of the particulate filter portion 39 are two layers of 0.5 micron filtration fiberglass pads 47 and 49, respectively. The material from these pads are prevented from leaving the filter assembly 11 through the outlet bell 17 by an aluminum screen 51 supported by a larger mesh aluminum support member 53 attached at its periphery in the inner surface 55 of the upstream section 57 of the bell section. Experience has shown that aluminum screen 51 and member 53 is not always needed. The inner surface dimensions of the inner surface 55, and the corresponding surface of the inlet bell 15 are adapted to be fixedly attached to the inlet polyurethane gasket 59 and the outlet polyurethane gasket 65 respectively by the application of hot glue or other suitable adhesive to the respective inlet 63 end and the outlet end 65 of the cylindrical canister member 19.

In operation, contaminated air (smoke plume) evacuated under suction by conventional means such as a motor/fan unit from the surgical site enters the filter 11 by means of appropriately dimensioned disposable smooth-bore vacuum flexible tubing (not shown) attached to the smaller diameter inlet portion 67 of the inlet bell 15. This smoke plume then is drawn through the plastic screen 23, the polyurethane pad 27 and the first layer of activated virgin coconut charcoal 29 before being deflected laterally by the member 37 concentrically disposed on the aluminum screen 35. This lateral deflection forces the smoke more uniformly throughout the second, relatively much thicker, layer of activated virgin coconut charcoal 31 for a more complete filtering of the objectionable odor associated with laser tissue burning than could be accomplished without such a unique deflection technique.

After leaving the second charcoal filter section, the laser smoke passes through the second polyurethane filter pad 43 to remove relatively smaller gross particles of vaporized tissue and other material. Finally, the laser smoke, according to this embodiment of the invention, passes through two layers of 0.5 micron filtration fiberglass pads 47 and 49 before flowing from the filter system 11 via the aluminum screen 51, the larger mesh aluminum screen 53, and the downstream end 69 of the bell section 17.

From the foregoing it should be evident that there has herein been described a new and improved laser smoke particulate/odor filter system that is usable in a laser smoke evacuation system for surgical procedure environments and which efficiently and economically removes odor and particulate matter including fat, carbon, cells, microorganisms, and smoke particles which are by-products from laser surgery.

In order to make the filter as efficient as possible, it is necessary to have an efficient dispersion of the flow of air in the charcoal element in order to prolong the life of the filter and make it as efficient as possible. The filter 21, screen 23 and pad 27 act as a first dispersion unit to disperse the air through the first charcoal filter 29 while the screen 35 and pad 37 disperse the flow of air throughout the second charcoal filters 31.

Dispersion is achieved by particulate loading the center portion of the polyurethane pad 27 in filter 21, and by the disk pad 37 on screen 35, causing the smoke to disperse through the charcoal filters 29 and 31 respectively.

Figure 8:
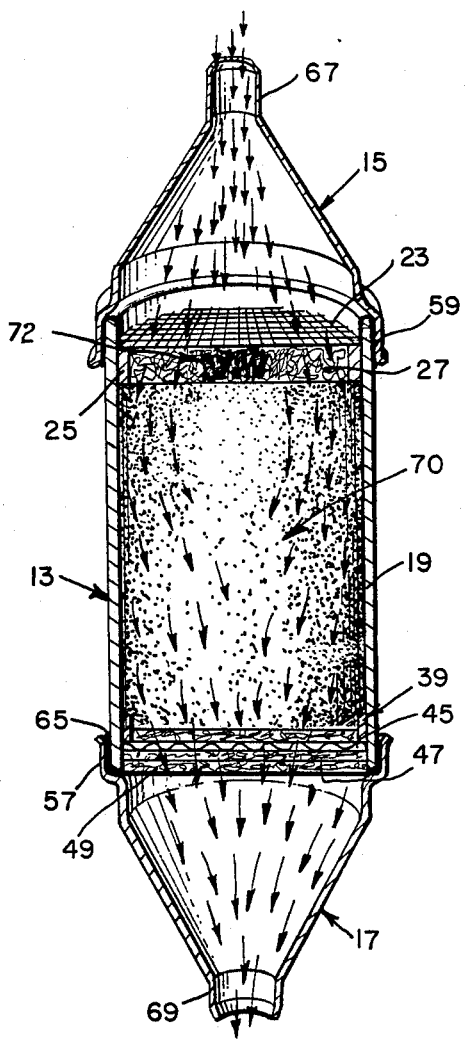
FIG. 8 is an elevational view, shown in perspective section, of the laser smoke particulated/odor filter system shown in FIG. 1 and illustrating the second embodiment.
Figure 7:
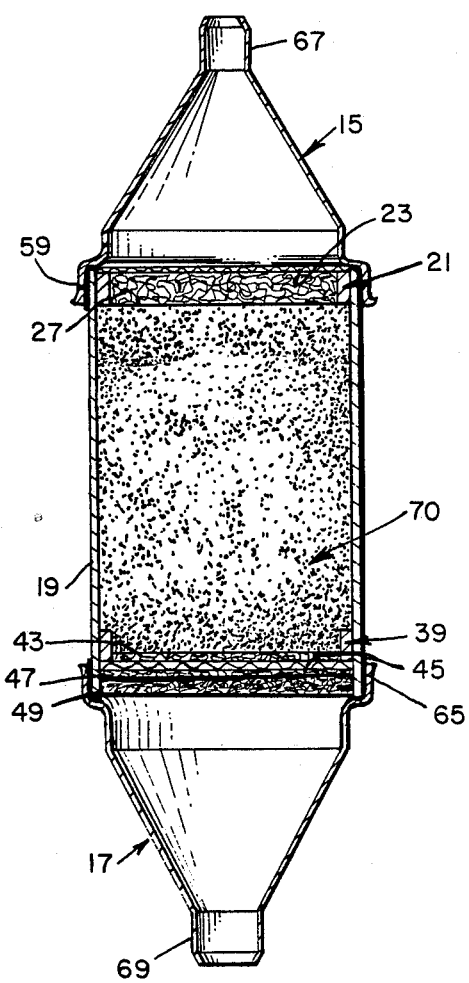
FIG. 7 is a sectional view taken along lines 4—4 of FIG. 1 and illustrating the second embodiment.

Referring now to FIGS. 1, 3, 6, 7 and 8, there is shown another embodiment of the filter applicable to surgical situations where the percentage of gross particulate is high which eliminates the need for the dispersion member 33 located between charcoal filters 29 and 31 as illustrated in FIGS. 2, 7 and 8. This second embodiment utilizes only one dispersion member and only one charcoal adsorption filter thereby lowering the cost of manufacture and at the same time, achieving excellent dispersion of the flow pattern within the single charcoal filter.

In describing the second embodiment of FIGS. 1, 3, 6, 7 and 8, similar numbers are used as in describing the first embodiment of FIGS. 1, 2, 3, 4 and 5 since the canisters are the same size and the only difference is within the canister.

The external characteristics and size of the second embodiment as illustrated in FIGS. 1 and 3 are the same as described for the first embodiment. As shown in FIG. 6, the gross particulate filter portion 21 has a plastic screen 23 mounted on a compressed paper ring 25 in which is disposed a polyurethane pad 27 as previously described. Downstream from the gross particulate filter 21 is a single charcoal filter member 70 consisting of virgin coconut charcoal that is approximately 6 inches deep and which substantially fills the canister member 19 illustrated in FIG. 3.

The charcoal filter 70 is retained within the cylinder 19 by a downstream gross particulate filter portion 39 which includes a ring 41, a polyurethane pad 43, and a plastic screen 45 disposed within the ring 41 as previously described.

In contact with the screen 45, are two layers of fiberglass pads 47 and 49, respectively. The periphery of pads 47 and 49 are bonded to the inside diameter of the cylindrical canister member 19 preferably by hot glue, so as to form a unitary structure. This procedure eliminates the need for the small screen 51 and the large screen 53 as illustrated in connection with FIG. 2.

The inner surface dimension of the inner surface 55 and the corresponding surface of the inlet bell 15 are adapted to tightly fit, and in the preferred embodiment, are glued together by hot glue or other suitable adhesive as the final step of the assembly.

In the preferred embodiment, it has been found preferable to fixedly attach the inlet bell 15 to the canister by means of hot glue or other suitable adhesive in the same fashion as the outlet bell 17 is attached to the canister. In this fashion, the complete filter can be removed and destroyed by incineration after use without fear of contamination by the handler or user.

Referring now to FIGS. 7 and 8, there is illustrated a cross-sectional view of the improved second embodiment more fully illustrating the single charcoal filter portion 70 and the fact that screens 51 and 53 have been eliminated from the outlet bell 17 and also that the internal pad 37 and screen 35 has been removed from the canister 19.

The filter 21 together with pad 27 located at the input side of filter member 70 performs the dispersion function for the complete filter member 70 thereby eliminating the need for two dispersion members one for each charcoal filter portion.

Referring now to FIG. 8 there is shown a build up of particulate 72 on filter pad 27 which results after the filter is initially placed in use. The particulate build up 72 causes the smoke plume to flow around the build up thereby effectively dispersing the smoke plume about the filter 21 and the charcoal filter 70.

Although the invention has been described in detail with respect to presently preferred embodiments of the invention, it should be understood that the invention may be practiced using similar functioning but different elements under the scope of the appended claims.

What is claimed is:

1. A laser smoke particulate/odor filter system usable in a laser smoke evacuation system for surgical procedure environments, including:
a generally cylindrical hollow housing having a gas inlet and an opposite gas outlet and defining within said housing a gas path therebetween;
at least one particulate filter portion supported in said housing adjacent said inlet in said gas path;
a first charcoal odor adsorption portion supported in said housing downstream of said aforementioned particulate filter portion in said gas path;
a second charcoal odor adsorption portion supported in said housing downstream of said first charcoal odor adsorption portion in said gas path; and
a smoke dispersion member supported in said housing between said first and second charcoal odor adsorption portions in said gas path, said dispersion member being a perforated screen having a central impervious disc.

2. The laser smoke particulate/odor filter system according to claim 1, wherein said second charcoal odor adsorption portion is relatively larger than said first charcoal odor adsorption portion.

3. The laser smoke particulate/odor filter system according to claim 1, wherein said screen lies in a plane generally orthogonal to said path.

4. The laser smoke particulate/odor filter system according to claim 1, also including a 0.5 micron filtration fiberglass portion disposed downstream of said second charcoal odor adsorption portion.

5. The laser smoke particulate/odor filter system according to claim 1, wherein said odor adsorption portions are of activated virgin coconut charcoal material.

6. The laser smoke particulate/odor fitler system according to claim 1, wherein said particulate filter includes an upstream gross particulate filter poriton, and a downstream particulate portion for removing smaller gross particles.

7. The laser smoke articulate/odor filter system according to claim 6, wherein said particulate filter portions are disposed on either side of said odor adsorption portions.

8. The laser smoke particulate/odor filter system according to claim 6, wherein said upstream and downstream particulate portions are polyurethane pads.

9. A laser smoke particulate/odor system usable in a laser smoke evacuation system for surgical procedure environments comprising:
- a generally cylindrical hollow housing having a gas inlet and an opposite gas outlet and defining within said housing a gas path therebetween;
- a single upstream particulate filter and dispersion portion supporting asid housing adjacent said inlet in said gas path for filtering said gas path and dispersing said gas path to thereby obtain a more uniform gas flow within said housing;
- a single charcoal odor absoprtion portion supported in said housing downstream of said aforementioned particulate filter portion in said gas path; and
- in which said upstream particulate filter and dispersion portion comprises a screen mounted on a compressed paper ring in which is disposed a pad.

10. A laser smoke particulate/oder filter system according to claim 9 which includes a pair of end bells with one fixedly connected to the gas inlet portion of said hollow housing and the other connected to the gas outlet portion of said hollow housing.

* * * * *